United States Patent
Kumar et al.

(10) Patent No.: US 9,210,933 B2
(45) Date of Patent: Dec. 15, 2015

(54) ANTIMICROBIAL PARYLENE COATINGS AND METHODS OF DEPOSITING SAME

(71) Applicant: SPECIALTY COATING SYSTEMS, INC., Indianapolis, IN (US)

(72) Inventors: Rakesh Kumar, Indianapolis, IN (US); Yingfei Ke, Carmel, IN (US); Dustin England, Zionsville, IN (US)

(73) Assignee: SPECIALTY COATING SYSTEMS, INC., Indianapolis, IN (US)

( * ) Notice: Subject to any disclaimer, the term of this patent is extended or adjusted under 35 U.S.C. 154(b) by 14 days.

(21) Appl. No.: 13/830,053

(22) Filed: Mar. 14, 2013

(65) Prior Publication Data
US 2013/0216599 A1    Aug. 22, 2013

Related U.S. Application Data

(63) Continuation-in-part of application No. 13/543,076, filed on Jul. 6, 2012, now abandoned.

(60) Provisional application No. 61/505,762, filed on Jul. 8, 2011.

(51) Int. Cl.
| | |
|---|---|
| *A01N 55/00* | (2006.01) |
| *A01N 25/34* | (2006.01) |
| *A61L 27/34* | (2006.01) |
| *A61L 27/54* | (2006.01) |
| *A61L 29/08* | (2006.01) |
| *A61L 29/16* | (2006.01) |
| *A61L 31/10* | (2006.01) |
| *A61L 31/16* | (2006.01) |

(52) U.S. Cl.
CPC ............... *A01N 55/00* (2013.01); *A01N 25/34* (2013.01); *A61L 27/34* (2013.01); *A61L 27/54* (2013.01); *A61L 29/085* (2013.01); *A61L 29/16* (2013.01); *A61L 31/10* (2013.01); *A61L 31/16* (2013.01); *A61L 2300/202* (2013.01); *A61L 2300/404* (2013.01); *A61L 2300/80* (2013.01)

(58) Field of Classification Search
None
See application file for complete search history.

(56) References Cited

U.S. PATENT DOCUMENTS

| | | | |
|---|---|---|---|
| 2007/0042198 A1* | 2/2007 | Schonemyr et al. | 428/447 |
| 2008/0075753 A1* | 3/2008 | Chappa | 424/426 |

FOREIGN PATENT DOCUMENTS

| | | | |
|---|---|---|---|
| EP | 1935355 A1 | | 6/2008 |
| NZ | 578314 | * | 3/2012 |
| WO | WO-2009151492 | * | 12/2009 |

OTHER PUBLICATIONS

Tan et al., "Surface Engineering and Patterning Using Parylene for Biological Applications", Materials, 2010, 3, 1818-1832.*

* cited by examiner

*Primary Examiner* — Ernst V Arnold
*Assistant Examiner* — Jianfeng Song
(74) *Attorney, Agent, or Firm* — Lando & Anastasi, LLP

(57) ABSTRACT

Antimicrobial parylene coatings and methods for their vapor-phase deposition.

10 Claims, 1 Drawing Sheet

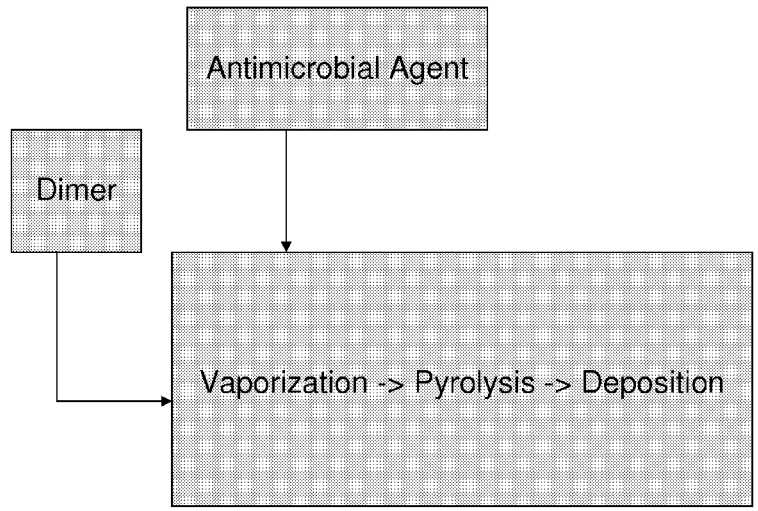

```
         ┌─────────────────────┐
         │ Antimicrobial Agent │
         └──────────┬──────────┘
                    │
┌───────┐           ▼
│ Dimer │  ┌──────────────────────────────────────────┐
└───┬───┘  │                                          │
    │      │  Vaporization -> Pyrolysis -> Deposition │
    └─────▶│                                          │
           └──────────────────────────────────────────┘
```

ANTIMICROBIAL PARYLENE COATINGS AND METHODS OF DEPOSITING SAME

CROSS-REFERENCE TO RELATED APPLICATIONS

This application claims the benefit under 35 U.S.C. §120 as a continuation-in-part of U.S. patent application Ser. No. 13/543,076, filed on Jul. 6, 2012, titled "ANTIMICROBIAL PARYLENE COATINGS AND METHODS OF DEPOSITING SAME," which claims priority under 35 U.S.C. §119(e) to U.S. Provisional patent application Ser. No. 61/505,762, filed on Jul. 8, 2011, titled "ANTIMICROBIAL PARYLENE COATINGS," the entire disclosure of each of which is hereby incorporated herein by reference in its entirety for all purposes.

FIELD OF THE DISCLOSURE

Aspects relate generally to parylene coatings and, more particularly, to antimicrobial parylene coatings and methods for their deposition.

SUMMARY

In accordance with one or more aspects, a method of forming an antimicrobial parylene coating may comprise immobilizing an antimicrobial agent on a parylene film through molecular attachment, interaction or covalent bonding.

In accordance with one or more aspects, a coating may comprise a parylene material and an antimicrobial agent immobilized on the parylene material.

Still other aspects, embodiments, and advantages of these exemplary aspects and embodiments, are discussed in detail below. Embodiments disclosed herein may be combined with other embodiments in any manner consistent with at least one of the principles disclosed herein, and references to "an embodiment," "some embodiments," "an alternate embodiment," "various embodiments," "one embodiment" or the like are not necessarily mutually exclusive and are intended to indicate that a particular feature, structure, or characteristic described may be included in at least one embodiment. The appearances of such terms herein are not necessarily all referring to the same embodiment.

BRIEF DESCRIPTION OF THE DRAWINGS

Various aspects of at least one embodiment are discussed below with reference to the accompanying figures, which are not intended to be drawn to scale. The figures are included to provide illustration and a further understanding of the various aspects and embodiments, and are incorporated in and constitute a part of this specification, but are not intended as a definition of the limits of the invention. Where technical features in the figures, detailed description or any claim are followed by references signs, the reference signs have been included for the sole purpose of increasing the intelligibility of the figures and description. In the figures, each identical or nearly identical component that is illustrated in various figures is represented by a like numeral. For purposes of clarity, not every component may be labeled in every figure. In the figures:

FIG. 1 presents a process schematic in accordance with one or more embodiments.

DETAILED DESCRIPTION

In accordance with one or more embodiments, parylene coatings with antimicrobial properties may be provided. In some embodiments, methods may introduce materials with antimicrobial properties into parylene films during a parylene deposition process. In at least some embodiments, parylene coating surfaces may be rendered substantially antimicrobial by adding and/or copolymerizing an antimicrobial agent into a parylene coating. Antimicrobial parylene films in accordance with one or more embodiments may be beneficial in circumstances where the performance properties of parylene films are desired in combination with an ability to control microbial growth on the film surface.

In accordance with one or more embodiments, a parylene coating may be applied to a substrate. The parylene coating may be a thin-film coating. The coating may be continuous and substantially uniform across a substrate. In some non-limiting embodiments, a parylene coating in a controlled thickness down to at least about several thousand angstroms may be achieved. A parylene coating in a controlled thickness up to at least about several millimeters may also be achieved. The thickness can generally be controlled to at least about plus or minus 10%. The parylene coating may be conformal with respect to surfaces, edges and crevices of a substrate and may be substantially pinhole-free. Multi-layer penetration may be achieved. In some embodiments, a parylene coating may add minimal dimension or mass to critical, weight-sensitive components. Parylene coatings may be optically clear, or incorporated with an indicator compound, such as a fluorescent, to facilitate identification.

In some embodiments, a parylene coating may be substantially biostable and biocompatible. The coatings may comply with biological testing requirements for ISO-10993. The coatings may comply with the biological testing requirements for USP Class VI plastics.

The coatings may promote proliferation of human cell types. In some embodiments, a parylene coating may exhibit barrier properties, such as may protect a substrate from fluids, moisture, chemicals and common gases. Protection from biofluids and biogases may be provided. A parylene coating may exhibit a high dielectric strength and/or may impart dry-film lubricity to a substrate. Parylene coatings may protect against corrosion, discoloration and contaminant entrapment. Parylene coatings may serve as dielectric barriers. In some embodiments, a parylene coating may be flexible, deter surface tackiness, and reduce the coefficient of friction. The parylene coating may have various coefficients of friction, for example, 0.15, 0.25 or 0.29 as measured by ASTM D 1894 for static observations. In some embodiments, a parylene coating may exhibit thermal and/or UV stability.

In accordance with one or more embodiments, the substrate may be any material, device or component to which it may be desirable to apply a coating, such as a barrier or functional layer. A parylene coating may be applied to virtually any surface material, including metals, elastomers, plastics, glasses, ceramics and papers. Parylene coatings may find applications in various industries including medical devices, electronics, automotive, military, aerospace, LEDs, and elastomers. In some embodiments, the substrate may be associated with electronics, printed circuit boards, printed circuit assemblies, sensors, detectors, LEDs, MEMS, capacitors, wafers, ferrite cores, fuel cells, digital displays, metal components. In other embodiments, the substrate may be a gasket or seal. In still other embodiments, the substrate may be a medical device.

In accordance with one or more embodiments, a parylene coating may be applied to an implantable or nonimplantable medical device. A medical device, such as but not limited to, a coronary stent, cerebral stent, cardiac assist device including pacemakers, electrosurgical tool, cochlear implant, ocular implant, mandrel, mold, catheter, elastomeric seal, needle, epidural probe or medical electronics may be coated with parylene. Parylene coatings may also be used as release agents for molds and forming devices, such as wire mandrels. The parylene coating may provide an acceptable surface for tissue contact and may protect the medical device and associated components. In some embodiments, a parylene coating may function as a surface primer, such as on a drug-eluting stent where a drug-containing copolymer is applied to a parylene coated metal coronary stent for human implantation. The parylene coating may enable integration of various drug and polymer combinations.

In accordance with one or more embodiments, a parylene coating may be produced by vapor-phase deposition and polymerization of para-xylylene (poly(p-xylylene)) or its substituted derivatives. The parylene coating may be made of any member of the generic parylene polymer series, or a variation thereof. Choice of a parylene polymer may be based on desired properties in view of an intended application. In some embodiments, a deposited parylene may be passive or reactive. In at least one embodiment, a deposited parylene may be halogenated. In some nonlimiting embodiments, parylene HT®, parylene N, parylene C or parylene D polymers commercially available from Specialty Coating Systems (Indianapolis, Indiana) as represented below may be deposited.

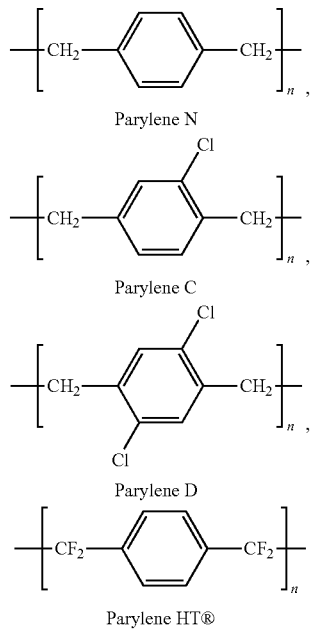

In accordance with one or more embodiments, a parylene coating may be antimicrobial. Any parylene material may be deposited in conjunction with an antimicrobial agent to form an antimicrobial parylene coating. In accordance with one or more embodiments, antimicrobial liquids or solids with suitable vapor pressures and thermal stability may be introduced into a coating chamber during a parylene coating process. In some embodiments, an attached receptacle containing the antimicrobial material may be heated, allowing vaporized antimicrobial material to pass into the coating chamber. The vaporized antimicrobial compound may be deposited on a substrate within the chamber simultaneously with a gaseous parylene monomer or in a layered approach. The amount and type of antimicrobial material used can be varied to suit a specific coating application. In some embodiments, one or more antimicrobial material(s) may be incorporated. In some nonlimiting embodiments, one or more antimicrobial compounds such as octadecyldimethyl(3-trimethoxysilylpropyl) ammonium chloride, 4-chloro-3,5-dimethylphenol, N-trimethoxysilylpropyl-N,N,N-trimethylammonium chloride, N,N-didecyl-N-methyl(3-trimethoxysilylpropyl) ammonium chloride, or similar compounds, may be added to parylene film as discussed herein.

In accordance with one or more embodiments, a parylene coating may be formed from a gaseous monomer without an intermediate liquid stage. A parylene coating may be applied at ambient temperature with vacuum deposition equipment. The film may grow over time as parylene polymer deposition occurs at a molecular level. A parylene coating may generally be applied in a room temperature vacuum chamber via a vapor deposition polymerization (VDP) process. Substrates to be coated may be placed into a coating chamber. A solid, granular dimer raw material may be heated under vacuum and vaporized into a dimeric gas. In some non-limiting embodiments, vaporization may be conducted at about 150° C. and about 1.0 torr. The gas may then be pyrolized to cleave the dimer to its monomeric form. In some non-limiting embodiments, pyrolysis may be conducted at about 680° C. and about 0.5 torr. The monomer gas may be deposited on a substrate as a polymer film in a deposition chamber at ambient temperature. The film may be as thin or thick as desired based on an intended application and substantially transparent. In some embodiments, the thickness may range from hundreds of angstroms to several millimeters. In at least some embodiments, a typical thickness may be in the microns range.

In accordance with one or more embodiments, antimicrobial compounds may be added to parylene films by various procedures as schematically illustrated in FIG. 1. In some embodiments, parylene and antimicrobial molecules may be combined in the vapor-phase to produce an antimicrobial parylene coating. A parylene film may be deposited on a substrate surface until a desired parylene film thickness is almost obtained. Near the end of the deposition cycle, heat sufficient to vaporize a desired antimicrobial compound may be applied to a receptacle containing the antimicrobial compound. This receptacle may be mounted to a coating chamber wall and may allow the passage of vaporized material into the coating chamber. An antimicrobial compound, such as but not limited to 4-Chloro-3,5-dimethylphenol, may be dissolved in a suitable carrier solvent to aid in distribution within the chamber. In some embodiments, the antimicrobial compound may be N,N-didecyl-N-methyl(3-trimethoxysilylpropyl) ammonium chloride. The vaporized antimicrobial compound may enter the coating chamber and be deposited simultaneously with the gaseous parylene monomer on the growing parylene film surface. The antimicrobial compound may be held in place through molecular entanglement with the parylene film near the film surface. In some embodiments, the antimicrobial agent(s) may be combined with parylene molecules through molecular attachment, interaction, and/or covalent bonding resulting in immobilization of the antimicrobial agent(s) on parylene coated surfaces.

In at least some embodiments, deposition may be carried out in a PDS 2060PC parylene deposition system commercially available from Specialty Coating Systems. Once parylene dimer and the desired antimicrobial compound have been added to the PDS, the system may be placed under vacuum. Parylene dimer may be sublimated by heating at reduced pressure and passed through a furnace where the dimer may be cleaved by pyrolysis and allowed to pass into the deposition chamber in the form of a gaseous monomer. The monomer may strike the surface of the desired substrate and spontaneously polymerize into a continuous film on the substrate. Antimicrobial compounds may be heated and introduced in gaseous form through a secondary port. If the antimicrobial compound is originally in solid form, such as 4-chloro-3,5-dimethylphenol, enough heat suitable to sublimate the compound, in some non-limiting embodiments between about 0° C. and about 190° C., may be applied. If the desired antimicrobial compound is in neat liquid form or in solution, such as octadecyldimethyl(3-trimethoxysilylpropyl) ammonium chloride, the liquid may be heated at an appropriate rate based on the solvent in order to avoid rapid boiling. Standard parylene deposition process conditions, including temperature and pressure, may be implemented in accordance with one or more embodiments. Antimicrobial agents may be integrated in parylene deposition processes as discussed herein.

In some embodiments, introduction of the gaseous antimicrobial compound can be performed concurrently with the introduction of gaseous parylene monomer or in an alternating fashion. In some nonlimiting embodiments, parylene may be deposited onto a substrate until a first thickness is obtained. Antimicrobial agent may then be introduced and deposited concurrently with parylene until a second thickness is obtained. Optionally, a parylene topcoat may be applied to the antimicrobial layer. If desired, a second parylene film deposition may be carried out to deposit a thin parylene film on top of the antimicrobial layer in order to control the rate of elution, if any, of the antimicrobial compound from the parylene film surface.

In accordance with one or more embodiments, relative thickness between layers and overall coating thickness may vary depending on desired properties and intended application. In some nonlimiting embodiments, a layer of parylene about 0.5 to about 25 microns in thickness may be deposited prior to introduction of antimicrobial agent. In some nonlimiting embodiments, a layer including antimicrobial agent may be about 50 angstroms to about 5 microns in thickness. In some nonlimiting embodiments, an optional parylene topcoat may be about 0.1 micron to about 2 microns in thickness.

Components to be coated may require only minimal vacuum tolerance. In at least some embodiments, there is no solvent, catalyst, plasticizer, cross-linking, elevated temperature or UV cure cycle involved in the coating process. In some embodiments, a substrate may be pretreated to promote optimal adhesion of parylene. In some embodiments, an A-174 silane treatment may be used. Other adhesion promotion technologies may be used in conjunction with the deposition methods. Substrate precleaning and cleanroom environments may also be implemented. Fixturing and masking techniques may be used to minimize contact points and avoid coating of areas to remain uncoated.

The function and advantages of these and other embodiments will be more fully understood from the following non-limiting examples. The examples are intended to be illustrative in nature and are not to be considered as limiting the scope of the embodiments discussed herein.

EXAMPLE 1

Octadecyldimethyl(3-trimethoxysilylpropyl)ammonium chloride was heated at an appropriate rate to achieve vaporization while avoiding rapid boiling. The vaporized antimicrobial material striked the parylene film surface and became anchored to the parylene film through molecular entanglement, hydrogen bonding or covalent bonding depending on the functional groups present in the desired antimicrobial compound and/or on the parylene film surface. Once deposition of parylene film and the desired antimicrobial compound was complete and the PDS returned to base pressure, the vacuum was released and the system was allowed to return to room pressure.

EXAMPLE 2

The presence of antimicrobial materials within the deposition chamber was confirmed by a quartz crystal monitoring system attached to the deposition chamber wall. Confirmation of the presence of antimicrobial materials on the surface of parylene films was determined by visual examination and FT-IR analysis. Test samples coated with parylene HT® and a layer of octadecyldimethyl(3-trimethoxysilylpropyl)ammonium chloride on top of the parylene film (Formulation 1), as well as samples coated with an additional thin parylene film on top of the antimicrobial layer (Formulation 2), were tested for antimicrobial efficacy against *E. coli, S. aureus, P. aeruginosa* and *C. albicans* per JIS Z 2801, Antibacterial Products—Test for Antibacterial Activity and Efficacy. Individual test samples and parylene HT® coated control samples were inoculated with a quantitative amount of the respective microorganism in a nutritive broth. A sterile plastic film was placed on top of the inoculated surface in order to spread the inoculum evenly and allow it to maintain contact with the sample surface. For each microorganism, the number of CFU/coupon was determined for half of the parylene HT control samples immediately after inoculation to identify the zero hour concentration. The other half of the inoculated parylene HT control samples and all Antimicrobial parylene HT samples were allowed to incubate for 24 hours at 36 ° C., after which the concentrations of the remaining microorganisms were determined. All sample groups were tested in triplicate. The detection limit of testing was 5 Colony Forming Units (CFU). Results of testing are shown in Table 1 for slides coated with two Antimicrobial parylene formulations.

TABLE 1

| Micro-organism | Sample Group | Sample Rep | Initial CFU/Coupon (Control, 0 h) | Control-CFU/Coupon (24 h) | Sample-CFU/Coupon (24 h) | | Average log Reduction vs. Control (24 h) |
|---|---|---|---|---|---|---|---|
| | | | | | Formulation 1 | Formulation 2 | |
| *E. coli* | A | 1 | 1.38E+05 | 6.15E+06 | <5 | <5 | >5.91 |
| | | 2 | 1.37E+05 | 1.60E+05 | <5 | <5 | |
| | | 3 | 1.36E+05 | 5.80E+06 | <5 | <5 | |
| *S. aureus* | B | 1 | 2.00E+05 | 8.95E+06 | <5 | <5 | >6.25 |
| | | 2 | 1.90E+05 | 9.25E+06 | <5 | <5 | |
| | | 3 | 1.55E+05 | 8.55E+06 | <5 | <5 | |

TABLE 1-continued

| Micro-organism | Sample Group | Sample Rep | Initial CFU/Coupon (Control, 0 h) | Control-CFU/Coupon (24 h) | Sample-CFU/Coupon (24 h) | | Average log Reduction vs. Control (24 h) |
|---|---|---|---|---|---|---|---|
| | | | | | Formulation 1 | Formulation 2 | |
| P. aeruginosa | C | 1 | 1.40E+05 | 1.40E+07 | <5 | <5 | >6.45 |
| | | 2 | 1.49E+05 | 1.64E+07 | <5 | <5 | |
| | | 3 | 1.53E+05 | 1.20E+07 | <5 | <5 | |
| C. albicans | D | 1 | 1.27E+05 | 5.30E+05 | <5 | <5 | >4.99 |
| | | 2 | 1.65E+05 | 4.00E+05 | <5 | <5 | |
| | | 3 | 1.57E+05 | 5.36E+05 | <5 | <5 | |

As can be seen, the sample readings for both Formulation 1 and Formulation 2 were <5 CFU/coupon after 24 hours which reflected a significant growth reduction in comparison to the control.

Those skilled in the art would readily appreciate that the various parameters and configurations described herein are meant to be exemplary and that actual parameters and configurations will depend upon the specific application for which the present disclosure are used. Those skilled in the art will recognize, or be able to ascertain using no more than routine experimentation, many equivalents to the specific embodiments described herein. It is, therefore, to be understood that the foregoing embodiments are presented by way of example only and that, within the scope of the appended claims and equivalents thereto, the disclosed coatings and deposition methods may be practiced otherwise than as specifically described. The present coatings and techniques are directed to each individual feature or method described herein. In addition, any combination of two or more such features, apparatus or methods, if such features, apparatus or methods are not mutually inconsistent, is included within the scope of the present disclosure.

While exemplary embodiments of the disclosure have been disclosed many modifications, additions, and deletions may be made therein without departing from the spirit and scope of the disclosure and its equivalents, as set forth in the following claims. It is to be appreciated various alterations, modifications, and improvements will readily occur to those skilled in the art. Such alterations, modifications, and improvements are intended to be part of this disclosure, and are intended to be within the spirit and scope of the disclosure. For example, an existing coating, deposition equipment or deposition method may be modified to utilize or incorporate any one or more aspects of the disclosure. Thus, in some cases, embodiments may involve configuring existing processes or equipment to comprise an antimicrobial component. Accordingly, the foregoing description and drawings are by way of example only.

As used herein, the term "plurality" refers to two or more items or components. The terms "comprising," "including," "carrying," "having," "containing," and "involving," whether in the written description or the claims and the like, are open-ended terms, i.e., to mean "including but not limited to." Thus, the use of such terms is meant to encompass the items listed thereafter, and equivalents thereof, as well as additional items. Only the transitional phrases "consisting of" and "consisting essentially of," are closed or semi-closed transitional phrases, respectively, with respect to the claims. Use of ordinal terms such as "first," "second," "third," and the like in the claims to modify a claim element does not by itself connote any priority, precedence, or order of one claim element over another or the temporal order in which acts of a method are performed, but are used merely as labels to distinguish one claim element having a certain name from another element having a same name (but for use of the ordinal term) to distinguish the claim elements.

What is claimed is:

1. A method of forming an antimicrobial parylene coating, comprising:
   immobilizing an antimicrobial agent on a parylene film through molecular attachment, interaction or covalent bonding via vapor-phase deposition wherein the antimicrobial agent comprises octadecyldimethyl(3-trimethoxysilylpropyl)ammonium chloride or N,N-didecyl-N-methyl(3-trimethoxysilylpropyl)ammonium chloride.

2. The method of claim 1, wherein the parylene film comprises:

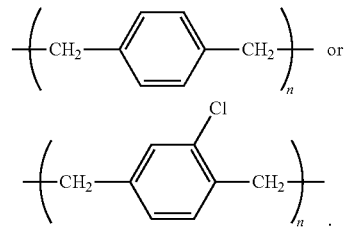

3. The method of claim 1, wherein the parylene film comprises:

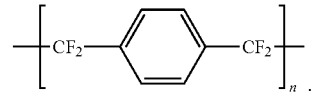

4. The method of claim 1, wherein the antimicrobial agent comprises N,N-didecyl-N-methyl(3-trimethoxysilylpropyl) ammonium chloride.

5. The method of claim 1, wherein the parylene film and the antimicrobial agent are deposited simultaneously on a substrate.

6. The method of claim 1, wherein the parylene film is deposited on a substrate prior to introduction of the antimicrobial agent.

7. The method of claim 1, further comprising depositing parylene on the immobilized antimicrobial agent.

8. The method of claim 1, further comprising dissolving the antimicrobial agent in a carrier solvent prior to immobilization.

9. The method of claim 1, wherein the substrate comprises a medical device.

10. The method of claim 9, further comprising pretreating the substrate prior to deposition.

\* \* \* \* \*